(12) United States Patent
Rajan et al.

(10) Patent No.: US 7,132,287 B2
(45) Date of Patent: Nov. 7, 2006

(54) METHOD FOR NEURAL STEM CELL DIFFERENTIATION USING 5HT-1A AGONISTS

(75) Inventors: Prithi Rajan, Rockville, MD (US); C. Anthony Altar, Garrett Park, MD (US)

(73) Assignee: Psychiatric Genomics, Inc., Gaithersburg, MD (US)

( * ) Notice: Subject to any disclaimer, the term of this patent is extended or adjusted under 35 U.S.C. 154(b) by 250 days.

(21) Appl. No.: 10/175,360

(22) Filed: Jun. 18, 2002

(65) Prior Publication Data

US 2003/0082802 A1 May 1, 2003

Related U.S. Application Data

(60) Provisional application No. 60/299,152, filed on Jun. 18, 2001.

(51) Int. Cl.
*C12N 5/02* (2006.01)
*C12Q 1/02* (2006.01)
*C12N 5/06* (2006.01)
*C12N 5/08* (2006.01)

(52) U.S. Cl. .................. 435/377; 435/29; 435/352; 435/363

(58) Field of Classification Search ................ 435/377; 514/724; 424/93.1
See application file for complete search history.

(56) References Cited

U.S. PATENT DOCUMENTS

| | | | |
|---|---|---|---|
| 5,753,506 A | 5/1998 | Johe et al. | 435/377 |
| 5,766,948 A | 6/1998 | Gage et al. | 435/368 |
| 5,851,832 A | 12/1998 | Weiss et al. | 435/368 |
| 6,103,530 A | 8/2000 | Carpenter et al. | 435/405 |
| 6,149,902 A | 11/2000 | Artavanis-Tsakonas et al. | 424/93.1 |

FOREIGN PATENT DOCUMENTS

| | | |
|---|---|---|
| WO | 97/08159 | 3/1997 |
| WO | 00/16777 | 3/2000 |
| WO | 01/34586 | 5/2001 |

OTHER PUBLICATIONS

Mattson MP. Stem cells as therapeutics for neurodegenerative disorders? Exp. Rev. Neurotherap. (2001), 1(2), 267-273.*
Kordower et al. Neuropathological evidence of graft survival and striatal reinnervation after the transplantation of fetal mesencephalic tissue in a patient with Parkinson's disease. N Engl J Med. Apr. 27, 1995;332(17):1118-24.*
Freeman et al. Bilateral fetal nigral transplantation into the postcommissural putamen in Parkinson's disease. Ann Neurol. Sep. 1995;38(3):379-88.*
Widner et al. Bilateral fetal mesencephalic grafting in two patients with parkinsonism induced by 1-methyl-4-phenyl-1,2,3,6-tetrahydropyridine (MPTP) N Engl J Med. Nov. 26, 1992;327(22):1556-63.*
Barker et al. Neural transplantation therapies for Parkinson's and Huntington's diseases. Drug Discov Today. Jun. 1, 2001;6(11):575-582.*
Lindvall et al. Stem cell therapy for human neurodegenerative disorders-how to make it work. Nat Med. Jul. 2004;10 Suppl:S42-50.*
Isacson O. The production and use of cells as therapeutic agents in neurodegenerative diseases. Lancet Neurol. Jul. 2003;2(7):417-24.*
Weissman IL. Translating stem and progenitor cell biology to the clinic: barriers and opportunities. Science. Feb. 25, 2000;287(5457):1442-6.*
Protais et al. Similar pharmacological properties of 8-OH-DPAT and alnespirone (S 20499) at dopamine receptors: comparison with buspirone. Eur J Pharmacol. Jul. 10, 1998;352(2-3):179-87.*
Zhou et al. Mechanisms governing the differentiation of a serotonergic phenotype in culture. Brain Res. Sep. 15, 2000;877(1):37-46.*
Vicario-Abejon et al. Hippocampal stem cells differentiate into excitatory and inhibitory neurons. Eur J Neurosci. Feb. 2000;12(2):677-88.*
Buznikov et al., "Serotonin and Serotonin-Like Substances as Regulators of Early Embryogenesis and Morphogenesis," *Cell Tissue Res.*, Aug. 2001, vol. 305, No. 2, pp. 177-186.
Chumasov et al., "Effect of Serotonin on Growth and Differentiation of Hippocampal Cells in Culture," *Neurosci. Behav. Physiol.*, Mar. 1980, vol. 10, No. 2, pp. 125-131.
Chubakov et al., "Effect of Serotonin on the Development of a Rat Cerebral Cortex Tissue Culture," *Neurosci. Behav. Physiol.*, Nov. 1986, vol. 16, No. 6, pp. 490-497.
Chubakov et al., "Effect of Serotonin on the Morpho-Functional Development of a Rat Cerebral Neocortex in Tissue Culture," *Brain Res.*, Mar. 1986, vol. 369, pp. 285-297.
Abe, "Therapeutic Potential of Neurotrophic Factors and Neural Stem Cells Against Ischemic Brain Injury," *Cereb. Blood Flow Metab.*, Oct. 2000, vol. 20, No. 10, pp. 1393-1408.

(Continued)

*Primary Examiner*—Daniel M. Sullivan
(74) *Attorney, Agent, or Firm*—Darby & Darby

(57) ABSTRACT

The present invention relates to a method for differentiating a neural stem cell into a neuronal cell such as a neuroblast or a neuron in vitro or in vivo. Particularly, the invention provides for a method for neural stem cell differentiation by contacting the neural stem cell with a 5HT1A ligand or agonist.

26 Claims, 4 Drawing Sheets
(2 of 4 Drawing Sheet(s) Filed in Color)

OTHER PUBLICATIONS

Ourednik et al., "Neural Stem Cells—A Versatile Tool for Cell Replacement and Gene Therapy in the Central Nervous System," *Clin. Genet.*, Oct. 1999, vol. 56, No. 4, pp. 267-278.

Lieske et al., "Effects of Serotonin on Neurite Outgrowth from Thalamic Neurons *In Vitro*," *Neuroscience*, Mar. 1999, vol. 90, No. 3, pp. 967-974.

Semkova et al., "Neuroprotective Effect of 5-$HT_{1A}$ Receptor Agonist, Bay X 3702, Demonstrated In Virto and In Vivo," *Eur. J. Pharmacol*, Oct. 1998, vol. 359, pp. 251-260.

Shetty and Turner, J Neurobiol. 1998;35:395-425.

Caldwell et al., Nat Biotechnol. 2001;19:475 9.

Mahlberg, et al., J Neurosci. 2000;20:9104-10.

Yocca, J Clin Psychipharmacology 1990;10(suppl., 3):6S-12S.

Durig et al., Dev Neurosci 2000; 11:833-837.

Lavdas et al., J Neurosci 1997; 17:7872-7880.

Jacobs et al., Mol Psychiatry 2000; 4:262-69.

Schuldiner et al., Brain Res 2001; 913:201-205.

* cited by examiner

A.

B.

CONTROL

BUSPIRONE

CONTROL

BUSPIRONE

METHOD FOR NEURAL STEM CELL DIFFERENTIATION USING 5HT-1A AGONISTS

This application claims priority from U.S. Provisional Application Ser. No. 60/299,152, filed Jun. 18, 2001, hereby incorporated herein by reference.

FIELD OF THE INVENTION

The present invention relates to methods for cell cultivation and differentiation. In particular, the invention relates to methods for cultivating and differentiating neural stem cells using ligands or agonists for the 5HT1A receptor.

BACKGROUND

Neural stem cells have been isolated from various regions of both rodent and human nervous systems and expanded in vitro as free floating aggregates (U.S. Pat. No. 5,851,832 to Weiss et al.) or as a monolayer attached to a substratum-coated dish (U.S. Pat. No. 5,753,506 to Johe). Neural stem cells are capable of extended self-renewal and have the ability, under appropriate conditions, to generate one or more subtypes of neurons and glia cells in vitro. By virtue of these properties, neural stem cells and their progeny can be applied for pharmaceutical drug discovery and for cell transplantation in neurological disorders.

The fate of neural stem cells can be controlled by a variety of extracellular factors. Growth factors such as basic Fibroblast Growth Factor (bFGF), Epidermal Growth Factor (EGF), Transforming Growth Factor (U.S. Pat. Nos. 5,851,832 and 5,753,506) and Leukemia Growth Factor (LIF; U.S. Pat. No. 6,103,530 to Carpenter) have all been shown to control the in vitro proliferation of neural stem cells. Growth factor expanded stem cells can differentiate into neuron and glia after mitogen withdrawn from the culture medium, but the proportion of neural stem cells that differentiate into neurons is minimal. However, the proportion of neural stem cells differentiating into the neuronal pathway can be increased by exposing the neural stem cells to various other growth factors such as Platelet Derived Growth Factor (PDGF; U.S. Pat. No. 5,753,506); bFGF (U.S. Pat. No. 5,766,948 to Gage and Jasodha); including neurotrophins such as Brain-Derived Growth Factor (BDNF; Shetty and Turner, J Neurobiol. 1998;35:395–425); Neurotrophin-3 (NT-3) and Neurotrophin-4 (NT-4; Caldwell et al., Nat Biotechnol. 2001;19:475–9); and Notch antagonists (U.S. Pat. No. 6,149,902 to Artavanis-Tsakonas et al.), to increase the quantity of neurons derived from a certain amount of neural stem cells.

For a variety of drugs used to treat psychiatric disorders, accumulating data from experimental studies are now providing novel insights into the mechanism by which the drugs produce their clinical effects. For example, preliminary data has indicated that treatment with the antidepressant drug fluoxetine increases neurogenesis in adult rat hippocampus (Mahlberg, et al., J. Neurosci. 2000;20:9104–10), which may be the reason for the delayed effects of the drug. In addition, numerous studies have shown that retinoic acid has similar differentiation effects in several mammalian systems, including rat, mouse and human embryonic stem cells and human neuroblastoma cells (Inatani et al., Brain Res 2001; 20:217; Guo et al., Electropheresis 2001; 22:3067; Jelitai et al, J Neurobiol 2002; 51:54–65; Lopez-Carballo et al., J Biol. Chem. PubMed ID: 12000752, e-publication ahead of print; Schuldiner et al., Brain Res 2001; 913:201–5; and Freemantle et al., Oncogene 2002; 21:2880–89). This suggests that diverse mammalian stem cells will be similarly affected by a specific compound or drug. However, further experimental data on the cellular mechanisms of action of drugs such as these are still needed, and a possible application of them outside of a clinical setting has, until now, remained unexplored.

The availability of large quantities of neuronal cells such as neurons or neuroblasts is important for the application of such cells both in vivo and in vitro, e.g., in cell transplantation therapy for neurodegenerative diseases and in vitro drug testing in psychiatric disorders. Such quantities can only be obtained by differentiation of cultured neural stem cells into these cell types, which requires large-scale cell culture using a significant amount of various growth factors and/or neurotrophins. Given the sparse availability of neural stem cells, especially human neural stem cells, the cost of growth factor and neurotrophin preparations, and the inability of some factors to cross the blood-brain barrier, there is a need for more efficient and economically viable strategies for differentiating neural stem cells into neuronal cells such as neuroblasts and neurons. This invention addresses these and other needs in the art.

SUMMARY OF THE INVENTION

The present invention is based on the surprising discovery that a 5HT1A ligand or agonist can be used for efficient differentiation of bFGF-expanded multi-potent neural stem cell or pluripotet progenitors or such cells capable of differentiating into neurons and neuroblasts. Accordingly, the present invention provides a method for promoting differentiation of neural stem cells into neuronal cell such as a neuroblast or a neuron, comprising contacting the neural stem cell with a 5HT1A ligand or agonist.

In one embodiment, the neural stem cell is exposed to a 5HT1A ligand or agonist at a concentration in the range of about 1 nM to about 1M, for a period of about 1 h to about 30 days. Preferably, the concentration of the 5HT1A ligand or agonist is about 1 mM, and the neural stem cell exposed to the 5HT1A ligand or agonist daily for a period of about 6 days. In another preferred embodiment, the concentration of the 5HT1A ligand or agonist is about 1 mM, and the neural stem cell exposed to the 5HT1A ligand or agonist daily for a period of about 2 days. In a third preferred embodiment, the concentration of the 5HT1A ligand or agonist is 1 mM and the exposure is 6 days.

In one preferred embodiment, the 5HT1A agonist is buspirone. In another preferred embodiment, the 5HT1A agonist is serotonin.

The present invention also provides for a method of promoting differentiation of neural stem cells into neuronal cells by contacting the neural stem cell not only with the 5HT1A ligand or agonist but also with one or more another differentiating agent such as Brain-Derived Neurotrophic Factor (BDNF). In one embodiment, the concentration of BDNF is 20 ng/ml.

The present invention also contemplates methods of treating CNS or PNS disorders characterized by neuronal damage in a mammal by administering a 5HT1A ligand or agonist to individuals in need thereof, or by transplantation of neurons that have been differentiated with a 5HT1A ligand or agonist in culture to individuals in need thereof.

The present invention further provides methods of screening for drugs that affect neuronal differentiation, or for producing highly differentiated neurons from stem cells. A culture with a high proportion of differentiated neurons derived from human stem cells can reproduce, to a certain extent, the degree of complexity of the human brain. These cultures can be used for drug screening for molecules that affect not only differentiation but also gene expression in CNS or PNS disorders involving neuronal damage or depletion. In the latter case, molecules identified can be used as lead compounds or new drug candidates to restore the expression of genes associated with the disorder to that of healthy neurons (or to bring it closer to that of healthy neurons).

In a related and more detailed aspect, the invention provides methods for screening for such molecules employing (i) a culture of stem cells derived from a primary culture of stem cells from an individual suffering from such a CNS or PNS disorder, and differentiating said culture using a 5HT1A ligand or agonist alone or in combination with other differentiating agents; and (ii) a culture of stem cells derived from a primary culture of stem cells from an individual suffering from such a CNS or PNS disorder.

In another related and more detailed aspect, the invention provides a method for screening for such molecules based on genes having different levels of expression in healthy and affected neurons which are associated with such disorders. Restoration of the expression level of one or more of such genes to (or close to) that of healthy neurons qualifies the test compound as a lead compound or new drug candidate.

Additional preferred aspects of the invention can be gleaned from the claims, the independent ones among them are incorporated by reference.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1A indicates the percent of neurons (TuJ1 positive) present in each of the populations. FIG. 1B shows the percentage of astrocytes in the same culture.

DETAILED DESCRIPTION OF THE INVENTION

Figure 1:
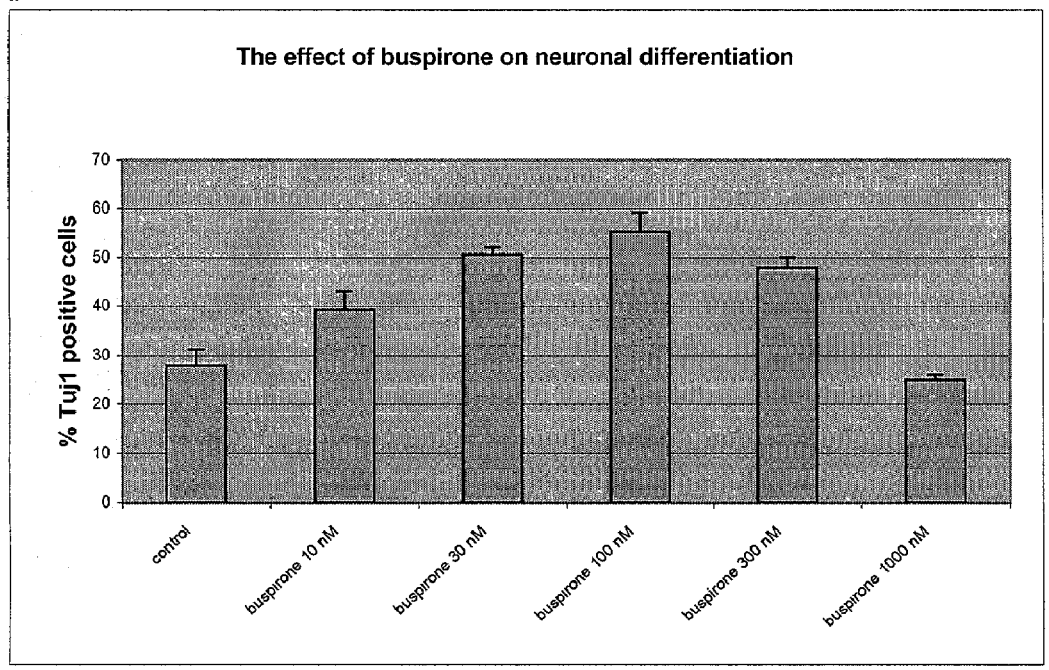
FIGS. 1A–B demonstrate the effect of buspirone on neuronal and astrocytic differentiation. Rat cerebellar stem cells were treated with buspirone at the given concentrations as described in the figure and in the results section. The cells were allowed to differentiate for about 6 days, followed by staining and counting as described.
Figure 1:
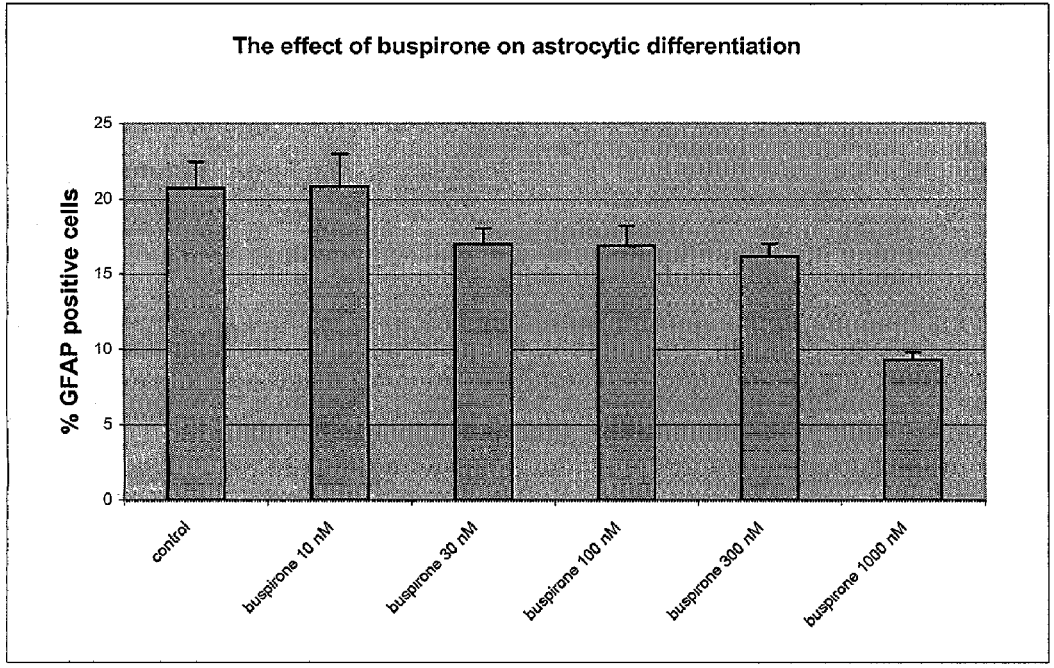

According to the present invention, neural stem cell differentiation can be stimulated by exposing the cells to ligands or agonists of the 5HT1A receptor, such as buspirone and serotonin. Buspirone is a small and inexpensive compound, readily available from commercial sources, which in contrast to most growth factors is stable in solution. As shown in the Examples, buspirone and serotonin promote neural stem cell differentiation into neurons, resulting in a culture enriched with neurons. These effects are observed on neural stem cells derived from the cortex, cerebellum, and striatum of mammalian embryos, such as rat. Since the effects can be prevented by concomitant treatment with a 5HT1A antagonist, the promotion of neuronal differentiation is mediated specifically via the 5HT1A receptor. Moreover, the combination of buspirone and BDNF is also effective for neural stem cell differentiation, whereas the presence of bFGF inhibits buspirone-mediated neuronal differentiation.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, the term "about" or "approximately" means within 50%, preferably 25%, more preferably 10%, and most preferably 5% of the given value. Alternatively, the term "about" means the standard deviation or variance for a given value, if available.

"Differentiation" is intended to encompass a process whereby a relatively unspecialized cell, e.g., a neural stem cell, acquire a specialized structural and/or functional feature that characterize a cell, tissue, or organ of a mature organism, or during a particular developmental phase if an organism. Examples of structural features include the expression of marker molecules by the cell, which may be identified using immunohistochemical staining procedures known in the art. In particular, antibodies specific for various neuronal or glial proteins may be employed to identify phenotypic properties of the differentiated cells.

The term "stem cell" refers to a cell that has the capacity to spontaneously differentiate into two or more subtypes of cells. A stem cell is capable of division to produce daughter cells that can be either new stem cells or further differentiated cells. Preferably, the stem cell is capable of self-maintenance, meaning that with each cell division, one daughter cell will also be a stem cell. A "totipotent" stem cell is capable of differentiating into all tissue types, including cells of the meso-, endo-, and ectoderm. A "multipotent" stem cell is a cell which is capable of differentiating into at least two of several fates.

A particular type of multipotent stem cell is a "neural stem cell", which is a stem cell of the nervous system that is capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, i.e. cells committed to become one or more types of neurons and glial cells respectively. Markers indicating that a cell is a neural stem cell include nestin. Generally, a neural stem cell does not express the following markers: neurogenin, neuron specific enolase ("NSE"), neurofilament, tau, β tubulin III, microtubule-associated protein 2a and b (MAP-2), Neu N, HuD (RNA binding protein), GFAP, Galactocerebroside, O4, and myelin proteins.

A "progenitor cell" or "precursor cell", used interchangeably herein, is a stem cell progeny that is committed to a particular differentiation pathway. A progenitor/precursor cell has the capability to proliferate, but to a more limited degree than a stem cell. For example, a particular type of progenitor cell is a "neuroblast", which is committed to becoming a neuron but is not yet a mature neuron. Other types of progenitor/precursor cells derived from neural stem cells include cells committed to the glial pathway, i.e., astroblasts, which are committed to becoming astrocytes (type I and type II); and bipotent precursors that can become either neurons or astrocytes, neurons or oligodendrocytes, or oligodendrocytes or astrocytes. Schwann cells and oligodendrocytes differentiate from the latter cell types.

A "neuron" is a cell which is the progeny of or derived from a neuroblast, a bipotent precursor and/or a neural stem cell. A neuron can be post-mitotic, i.e., non-proliferative. For example, a neuroblast or progenitor cell can convert directly into a neuron, or proliferate in the presence of a mitogen (e.g., bFGF) and then convert into a postmitotic neuron. Neurons are specialized for the transmission of nerve impulses. Each neuron consists of an enlarged portion, the cell body or perikaryon containing the nucleus and from which a variable number of thread-like processes, called dendrites, project. A neuron may also contain a single nerve fiber or axon which conveys impulses away from the body. Neurons may be identified using visual inspection or immunohistochemistry with antibodies to neuron specific enolase ("NSE"), neurofilament, tau, β-tubulin III, microtubule-associated protein 2A and B (MAP-2), Neu N, HuD (RNA binding protein) or other known neuronal markers. Generally, neurons are nestin-negative.

The central nervous system or CNS the part of the nervous system which in vertebrates consists of the brain and spinal cord, to which sensory impulses are transmitted and from which motor impulses pass out, and which supervises and coordinates the activity of the entire nervous system.

The peripheral nervous system or PNS is the part of the nervous system that is outside the central nervous system and comprises the cranial nerves excepting the optic nerve, the spinal nerves, and the autonomic nervous system. A disorder affecting the neurons within the CNS or PNS is a "neurological disorder."

The term "psychiatric disorder" or "neuropsychiatric disorder", which may also be referred to as a "major mental illness disorder" or "major mental illness", refers to a disorder which may be generally characterized by one or more breakdowns in the adaptation process. Such disorders are therefore expressed primarily in abnormalities of thought, feeling and/or behavior producing either distress or impairment of function (i.e., impairment of mental function such with dementia or senility). Currently, individuals may be evaluated for various neuropsychiatric disorders using criteria set forth in the most recent version of the American Psychiatric Association's Diagnostic and Statistical Manual of Mental Health (DSM-IV). Exemplary psychiatric disorders include, but are not limited to, schizophrenia, attention deficit disorder (ADD), schizoaffective disorder, bipolar disorder, bipolar affective disorder, unipolar affective disorder, adolescent conduct disorder, autism, depression, and anxiety disorders.

A "neurodegenerative disease" is a disease which progressively degenerates neurons or neuronal function. Examples of neurodegenerative diseases include all forms of senile dementia including chronic disorders such as Alzheimer's disease and Huntington's Chorea, Parkinson's disease, amyotrophic lateral sclerosis, and acute disorders such as stroke, schizophrenia, epilepsy, and injury of the brain, peripheral nerves or spinal cord.

A mammal refers to any of the higher vertebrate animals comprising the class Mammalia, including but not limited to humans and non-human animals.

"Non-human animals" include, without limitation, laboratory animals such as mice, rats, rabbits, hamsters, guinea pigs, etc.; domestic animals such as dogs and cats; and, farm animals such as sheep, goats, pigs, horses, and cows. A non-human animal of the present invention may be a mammalian or non-mammalian animal; a vertebrate or an invertebrate.

Buspirone (CAS Registry No. 36505-84-7) is also known as Buspar, and 8-[4-[4-(2-pyrimidinyl)-1-piperazinyl]butyl]-8-azaspiro[4,5]decane-7,9-dione. As used herein, the term includes physiologically acceptable salts such as buspirone hydrochloride.

Serotonin (CAS Registry No. 50-67-9D) is also known as (5-hydroxytryptamine or 5-HT) (CAS Registry No. 50-67-9). Serotonin is a naturally occurring chemical that is widely distributed in the body, including the brain. Large concentrations of 5-HT are found in the gastrointestinal tract and in platelets.

Ipsapirone is closely related to buspirone and is currently in clinical trials.

8-hydroxy-2-(di-n-propylamino)tetralin, known as 8-hydroxy-DPAT, has the formula $C_{16}H_{25}NO$ (CAS Registry No. 900004-85-5) is a well known 5HT1A agonist.

Gepirone (CAS Registry No. 83928-76-1] having the formula $C_{19}H_{29}N_5O_2$ and a molecular weight of 359.47 g/mol, is a pyridinyl piperazine 5-HT1A receptor agonist. Mechanism of action studies have demonstrated that gepirone, compared to buspirone, possesses a much greater selectivity for 5-HT1A receptors over dopamine D2 receptors. Long-term studies have shown that gepirone has a differential action at presynaptic (agonist) and post-synaptic (partial agonist) 5-HT1A receptors.

Sumatriptan (sumatriptan succinate-3-[2-(dimethylamino)ethyl]-N-methyl-indole¾5-methanesulfonamide succinate-CAS Registry No. 103628-46-2) has an empirical formula $C_{14}H_{21}N_3O_2S.C_4H_6O_4$, representing a molecular weight of 413.5.

5-methoxy-N,N-dimethyltryptamine (5-MeO-DMT-CAS #: 1019-45-0, has a molecular formula of $C_{13}H_{18}N_2O$ and is an indole alkaloid substance that occurs in a variety of leguminoceae genera, and is a hallucinogen. It is has high affinity for the 5HT1A receptor.

Oxymetazoline hydrochloride (3-[(4,5-dihydro-1H-imidazol-2-yl) methyl]-6-(1,1-dimethylethyl)-2,4-dimethylphenol) has a M.W. 296.84 and has partial 5HT1A agonist activity.

U-92016A [(+)-R)-2-cyano-N,N-dipropyl-8-amino-6,7,8,9-tetrahydro-3H-benz[e]indole] is 5-HT1A receptor agonist with an exceptionally high degree of intrinsic activity.

MDL 72832 or 5-methylurapidil or 8-[4-(1,4-benzodioxan-2-yl-methylamino)butyl]-8-azaspirodecane-7,9-dione is a partial 5HT1A agonist.

As used herein, "receptor" refers to a macromolecular binding site (usually a protein, which may also be glycosylated or phosphorylated) which is at least partially exposed on the surface of a cell, and which has specific and limited affinity for one or more fluid-borne molecules, called "ligands" (these usually are neurotransmitters or hormones). When a ligand contacts an appropriate receptor, a brief binding reaction occurs which causes a cellular response, such as opening of an ion channel, which leads to activation and depolarization of the neuron. Most receptor molecules are proteins which straddle the membrane of a cell, with an external portion for binding reactions, and an internal portion which helps carry out the cellular response that occurs when the receptor is activated by a ligand.

As used herein, the term "ligand" applies to any identifying compound or ligand or their competitors and includes, but is not necessarily limited to the functional categories of agonist, partial agonist and antagonist. An "agonist" is defined as a ligand that promotes the normal biological function of the receptor when it competes successfully with the normal endogenous ligand (5HT or serotonin) for binding to the receptor. A "partial agonist" binds as does the agonist, but promotes only partial receptor function. An "antagonist" inhibits all receptor function with its binding to the receptor in competition with the normal, endogenous agonist.

The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. Physiologically acceptable means any solvent or solution consisting of components that are physiological and non-toxic, such as buffered salt solutions. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "effective dose" refers to that amount of a compound or compositions that is sufficient to result in a desired activity. Thus, and effective dose of a 5HT1A agonist would be the dose sufficient to induce differentiation of neural stem cells to express preferentially a neuronal phenotype. For a substance administered to a subject, a "effective amount" for administration is that creating a sufficient concentration of the active ingredient or a metabolite thereof at the target site e.g., in the vicinity of a neural stem cell of said subject.

In accordance with the present invention, there may be employed conventional molecular biology, microbiology and recombinant DNA techniques within the skill of the art. Such techniques are explained fully in the literature. See, for example, Sambrook, Fitsch & Maniatis, Molecular Cloning: A Laboratory Manual, Second Edition (1989) Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins, eds. 1984); Animal Cell Culture (R. I. Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994).

In addition, various methods for culture and differentiation of CNS cells may be used in accordance with the present invention. Such methods are also explained fully in the literature. See, for example, "Protocols For Neural Cell Culture", (Federoff and Richardson, eds., Humana Press, Totova, N.J., 1997) and "Culturing Nerve Cells (Banker and Goslin, eds., the MIT Press, Cambridge, Mass., 1998).

Preparation and Expansion of Neural Stem Cells

Multipotent neural stem cells can be obtained from embryonic, fetal, post-natal, juvenile or adult neural tissue. The experiments described here were performed exclusively on fetal stem cells. The neural tissue can be obtained from any animal that has neural tissue such as insects, fish, reptiles, birds, amphibians, and mammals. The preferred source of neural tissue is from mammals, preferably rodents and primates, and, most preferably, rats and humans. Typically, extracted neural tissue sample is placed into an appropriate medium such as HBSS without divalent cations, buffered with HEPES and sodium bicarbonate-see Methods below. Next, tissue is dissociated into cells using enzymatic techniques (e.g., trypsinization) or gentle mechanical dissociation (e.g., trituration). The dissociated cells can then be cultured as neurospheres or as a monolayer using a suitable growth medium. For example, cells can be cultured in NSA medium (Euroclone, UK) or DMEM/F12 medium (described infra) complemented with one or more mitogens or growth factors such as, e.g., basic fibroblast growth factor (bFGF), epidermal growth factor (EGF), transforming growth factor-alpha (TGF), transforming growth factor-beta (TGF-$\beta$), and leukocyte inflammatory factor (LIF). In the case of monolayer culture, cells may be grown in the presence of bFGF on a plastic surface or in a dish pre-coated with a substrate to which the cells can attach. Such substrates include, but are not limited to, poly-ornithine and fibronectin. At regular intervals, the cells should be subcultivated or split to ensure a suitable cell density.

Differentiation of Neural Stem Cells

Neural stem cells can be differentiated into neurons using the method of the invention, i.e., contacting the neural stem cells with 5HT1A agonists. Such 5HT1A agonists include but are not limited buspirone and serotonin. Other agonists and partial agonists are listed below under the section entitled 5HT1A Ligands Agonists, and Antagonists.

Differentiation of a neural stem cell may be accomplished as follows. First, culture medium containing cell growth promoting factors should be replaced with a medium which does not contain mitogens growth factors etc., i.e., a "differentiation medium." In a preferred embodiment, this medium is serum-free medium supplemented with insulin, transferrin, and selenium. Next, a 5HT1A agonist is added to the differentiation medium. In an alternative embodiment, the 5HT1A agonist is already present in the differentiation medium. In one embodiment, the neural stem cell is exposed to a 5HT1A agonist at a concentration in the range of about 1 pM to about 1M, even more preferably in the range of 1 nM to 1 mM, for a period of about 1 h to at least 2 days. In a preferred embodiment, the concentration of the 5HT1A agonist is in the range of about 0.01 to about 10 µM, or, even more preferably, about 0.1 or 1 mM. In another preferred embodiment, the neural stem cell is exposed to the 5HT1A agonist for a period of at least 2 days, preferably about 6 days. In another preferred embodiment, brain-derived neurotrophic factor (BDNF) is also present in or added to the differentiation medium. The preferred concentration range of BDNF is from about 10 pg/ml to about 30 µg/ml, more preferably, the concentration of BDNF is about 20 ng/ml.

Preferably, the method of the invention provides neural stem cell cultures comprising at least about 30%, more preferably at least about 40%, and most preferably at least about 50% neuroblasts or neurons differentiated from a mammalian neural stem cell culture.

Evaluation of Neural Stem Cell Differentiation

Neural stem cell differentiation into a neuroblast or a neuron can be analyzed by either immunohistochemical techniques or visual inspection to assess the number of neuronal cells or neurons formed after conducting a differentiation assay. Alternatively, the relative proportion of neuronal cells, neuroblasts, or neurons to remaining neural stem cells, or total number of cells, may be estimated. For example, neural stem cells may be identified using immunohistochemistry with antibodies specific for a marker such as, e.g., nestin, and neurons may be identified using antibodies for neuron-specific markers such as, e.g., β-tubulin, NSE, neurofilament, tau, microtubule-associated protein 2A and B, Neu N, neurogenin, or other markers known in the art.

5HT1A Receptors, Ligands, Agonists and Antagonists

Serotonin is a well-characterized neurotransmitter which regulates calcium ion channels on the surface of nerve and muscle cells. There are several subtypes of receptor for brain serotonin, also known as 5-hydroxytryptamine or 5HT, including the 5HT1A, 5-HT1B, 5-HT1D, 5-HT1E, 5-HT1F, 5-HT2A, 5-HT2B, 5-HT2C, 5-HT3A/3B, 5-HT4A/4B, 5-HT5A/5B, 5-HT6 and 5-HT7A, 5-HT7B, 5-HT7C, and 5-HT7D receptor subtypes. All receptor subtypes are G-protein coupled receptors. Serotonin-1 A receptors are located on serotonin cell bodies in the mid-brain dorsal raphe (DR) nucleus, and the activation of these receptors inhibits the firing of serotonin neurons and diminishes the release of this neurotransmitter in the prefrontal cortex. Some serotonin receptor ligands are clinically approved as drugs for the treatment of migraine headaches, depression, high blood pressure, and psychosis. Serotonin is present at early stages of the developing brain, at the early states of neurogenesis, and the development of the serotonin pathway appears to coincide with neuronal proliferation and differentiation in the cortex (Levitt et al., Brain Res. 1979; 262:243058; Kalsbeek, J Comp Neur 1988; 269:58–72; Durig et al., Dev Neurosci 2000; 11:833–37; and Lavdas et al., J Neurosci 1997; 17:7872–7880). The present invention provides a novel method of using 5HT1A serotonin receptor agonists or ligands to differentiate neural stem cells into neurons.

Ligands to the 5HT1A subtype receptor are referred to as 5HT1A ligands. They are defined as any chemical compound, regardless of molecular structural type, that exhibits clearly measurable binding competition against established identifying serotonin receptor ligands that are documented to define the 5HT1A receptor subtype by selectivity and high affinity binding. This applies to receptor preparations derived from any biological source.

As used herein, the term "ligand" applies to any identifying compound or ligand or their competitors and includes, but is not necessarily limited to the functional categories of agonist, partial agonist and antagonist. An "agonist" is defined as a ligand that promotes the normal biological function of the receptor when it competes successfully with the normal endogenous ligand (5HT or serotonin) for binding to the receptor. A "partial agonist" binds as does the agonist, but promotes only partial receptor function. An "antagonist" inhibits all receptor function with its binding to the receptor in competition with the normal, endogenous agonist. Methods of measuring in vivo binding and affinity to 5HT1A receptors are described in Kung et al., Synapse 1994;18:359–66.

Known agonists for serotonin receptor subtype 5HT1A that can be used according to the present invention include any receptor that shows exclusive, high affinity to the agonist 8-hydroxy-DPAT (8-hydroxy-2-(di-n-propylamino) tetralin) as an identifying ligand. Both enantiomers are full agonists. Other high-affinity ligands selective for the 5HT1A receptor exist, for example, ipsapirone, 5-methoxy-N,N-dimethyltryptamine; 3-(2-Dimethylaminoethyl)-5-methoxy-indole (also referred to as 3-[2-(dimethylamino)ethyl]-5-methoxyindole; 5-Methoxy-DMT; and 5-OMe-DMT; available from Sigma); 1-[3-(3,4-Methylenedioxyphenoxy, (BP-554 maleate-available from Tocris Cookson, St. Louis, Mo.); 8-Hydroxy-DPAT hydrobromide (or 8-OH-DPAT/(±)-8-Hydroxy-2-dipropylaminotetralin, also available from Tocris Cookson) and sumatriptan (3-[2-(dimethylamino) ethyl]-N-methyl-indole⅗5-methanesulfonamide succinate).

5HT1A partial agonists include buspirone hydrochloride (N-(4-[4-(2-Pyrimidinyl)-1-piperazinyl]butyl)-8-azaspiro[4, 5]decane-7,9-dione-available from Sigma); MDL 72832 hydrochloride (8-[4-(1,4-Benzodioxan-2-ylmethylamino) butyl]-8-azaspiro[4.5]decane-7,9-dione-available from Tocris Cookson); S(−) pindolol ([1-(1H-indol-4-yloxy)-3-[(1-methylethyl)amino]-2-propanol]-available from Sigma), and U-92016A ([(+)-R)-2-cyano-N,N-dipropyl-8-amino-6,7,8,9-tetrahydro-3H-benz[e]indole]).

Buspirone ($C_{21}H_{31}N_5O_2$) is an anxiolytic drug belonging to a chemical class referred to as the azapirones. It is the first in the class of pure anxioselective agents and has been used for treatment of depression and anxiety related disorders, has been shown to act via the 5HT1A receptor (Yocca, J Clin Psychipharmacology 1990;10 (suppl., 3):6S–12S), and neurons are believed to be involved in mediating the effects of buspirone. However, the mechanism of action of the drug is not well characterized, but it may exert its effect by acting on the dopaminergic system in the central nervous system or by binding to serotonin receptors. Antagonists to the 5HT1A receptor include WAY 100635 maleate salt (N-[2-[4-(2-Methoxyphenyl)-1-piperazinyl]ethyl]-N-2-pyridinylcyclo-hexanecarboxamide-available from Sigma; S(−)-UH-301 HCl (also referred to as S(−)-5-Fluoro-8-hydroxy-2-dipropylamino-1,2,3,4-tetrahydronaphthalene hydrochloride or S(−)-5-Fluoro-8-hydroxy-DPAT hydrochloride-available from Sigma; p-MPPI HCl (4-Fluoro-N-(2-[4-(2-methoxyphenyl)1-piperazinyl]ethyl)-N-(2-pyridinyl)benzamide-Sigma); p-MPPF HCl (4-Fluoro-N-(2-[4-(2-methoxyphenyl)1-piperazinyl]ethyl)-N-(2-pyridinyl)benzamide-Sigma); methiothepin (1-[10,11-Dihydro-8-(methylthio)dibenzo[b,f] thiepin-10-yl]-4-methylpiperazine Metitepine-Sigma); NAN-190 hydrobromide (1-(2-Methoxyphenyl)-4-(4-[2-phthalimido]butyl)piperazine-Sigma); Spiroxatrine (8-[(2,3-Dihydro-1,4-benzodioxin-2-yl)methyl]-1-phenyl-1,3,8-triazaspiro[4,5]decan-4-one-Tocris Cookson); cyproheptadine hydrochloride sesquihydrate (Periactin-Sigma); ketansarin (3-(2-[4-(4-Fluorobenzoyl)-1-piperidinyl]ethyl)-2,4(1H, 3H)-quinazolinedione-Sigma); ritanserin (6-(2-[4-(Bis[4-fluorophenyl]methylene)-1-piperidinyl]-ethyl)-7-methyl-5H-thiazolo[3,2-a]pyrimidin-5-one-Sigma); MM 77 dihydrochloride (1-(2-Methoxyphenyl)-4-(4-succinimidobutyl) piperazine-Tocris Cookson); or tropisetron (also referred to as ICS-205,930 or endo-8-Methyl-8-azabicyclo [3.2.1]oct-3-ol Indol-3-yl-carboxylate-Sigma).

Applications

As described herein, the present invention provides a method to promote the differentiation of neural stem cells, preferably mammalian neural stem cells, into neurons employing 5HT1A agonists such as buspirone and serotonin. The invention also provides cell cultures enriched in neurons as compared to control cultures.

Neural stem cells provide the ideal in vitro system to prepare neuronal cells and to study neuronal differentiation. However, very few systems for efficient neuronal differentiation, whether in vivo or in vitro, have been found so far. The instant invention enables the differentiation of neurons of choice from stem cells originating from different regions of the brain. Furthermore, while most differentiation protocols so far have used exclusively growth factors, the invention offers a novel and economically advantageous concept in the field; the use of a small molecule that can promote neuronal differentiation.

The method to promote neuronal differentiation, and the enriched culture of differentiating or differentiated cells themselves, can be used for any purpose or application in which neuronal differentiation or a cell population enriched in neurons is desired. This section describes some exemplary application areas, such as in drug screening assays, and treatment of CNS disorders.

Drug Screening

For drug screening purposes, the method of the invention can be used, for example, to identify agents which modify the gene expression of differentiating or differentiated neurons, or which modify 5HT1A-mediated differentiation of neural stem cells. These assays can be conducted in vitro or in vivo model systems, using mice or other animals, or cultures of cells derived from neural stem cells.

Gene Expression Assays. Changes in gene expression associated with CNS disorders such as neuropsychiatric disorders or neurodegenerative disorders can provide significant insights into pathways of disease etiology or drug action, and also help identify novel targets for drug screening. Once a gene or a set of genes are known that are differentially expressed in a disease or disorder, and a correlation is established between a gene or a set of genes and a disease or disorder, defining a "disease signature", screening programs for drugs that revert the "disease signature" to a normal (or close-to-normal) expression pattern can be initiated even when the functions of an individual gene are not fully understood. The screening methods can use cultured cells to screen for candidate drug compounds or lead compounds. Preferably, the cells are ones having an expression profile that is typical of neuronal cells or, alternatively, they may be neuronal cells manipulated to produce an expression profile typical of cells of a particular CNS disorder. In a preferred embodiment, the cells are neurons that have been differentiated from neural stem cells using a 5HT1A agonist. The cells or cell lines used will also, preferably, give rise to reproducible changes in their gene expression profiles when contacted with known therapeutic drugs used to treat CNS disorders, such as antipsychotic drugs. In particularly preferred embodiment, these changes will be opposite changes that are observed in the disease signature. That is to say, in such embodiments genes (or their homologs) that are normally expressed at higher levels in the disease signature are preferably expressed at lower levels in cells or cell lines contacted with the known antipsychiatric drug, and vice-versa.

When a large number of drugs are to be screened for such a purpose, a high-throughput assay where the effect of many drugs on living cells are assessed simultaneously is a major advantage. In the prior art, however, these types of assays have been largely impeded by the lack of a reproducible source of large quantities of neuronal cells particularly neurons having normal gene signatures or in which gene signatures mimicking "disease signatures" can be implemented. These problems can now be addressed using the method of the invention.

One exemplary screening method contemplated for use in this invention is multi-parameter high-throughput screening, or MPHTS. This method is described in U.S. Provisional Application Ser. No. 60/349,936, filed Jan. 18, 2002, and in U.S. non-provisional application Ser. No. 10/175,523 filed Jun. 18, 2002, and entitled Multiple Paramater High-Throughput Screening Assay (MPHTS), commonly owned, both hereby incorporated by reference in their entirety. MPHTS can advantageously be used for screening for drugs or compounds that affect gene expression in neural cells to identify compounds that affect the disease signatures of CNS, neuropsychiatric, neurodegenerative, and/or other neurological disorders. Generally, an MPHTS assay based on cultures cells can involve the following gene expression systems.

First, as described above, "disease-signatures" are obtained or provided by measuring expression levels for a plurality of genes in cells or tissues derived from an individual having a neuropsychiatric disorder. In some instances, "disease-signatures" may be also created in cultured cells in vitro, by manipulating cultured normal cells to exhibit a known "disease signature".

Second, "normal" gene-signatures can be obtained or provided by measuring expression levels for a plurality of genes in cultured neuronal cells (e.g., in cultured neurons that are derived from neural stem cells differentiating or differentiated according to the method of the present invention). Thereby, the "disease-signatures" can be compared to expression levels in normal cells or tissues (i.e., brain cells or tissues from healthy individuals, not affected by a CNS disorder) to identify the particular genes that are differentially expressed in the CNS disorder of interest.

Third, "drug signatures" may also be obtained or provided by measuring expression levels for a plurality of genes in cultured neuronal cells or tissues that are treated with a therapeutic compound known to be effective for treating a CNS disorder. Exemplary drug signatures, which were obtained from both rat and human neuronal cells treated with therapeutic compounds, are provided in U.S. provisional patent application Ser. No. 60/349,936 filed on Jan. 18, 2001, and in U.S. non-provisional application Ser. No. 10/175,523, filed Jun. 18, 2002, and entitled Multiple Paramater High-Throughput Screening Assay (MPHTS) and incorporated herein by reference, in their entirety. Other drug signatures may be readily obtained by those skilled in the art.

Fourth, expression levels for the plurality of genes are obtained or provided in neuroblasts or neurons that are contacted with a test compound, i.e., a "drug candidate signatures", and these expression levels may then be compared to "disease signatures" and/or to "drug-signatures".

Generally speaking, the "drug candidate signature" is compared to the "normal" gene signatures to identify changes in the expression level(s) for particular genes. Similarly, the "drug-signature" is also compared to the "normal" gene signature, to identify particular genes whose expression levels change when the cells are contacted with the known therapeutic compound. Compounds that are determined to affect changes in the expression levels of particular genes are designated "lead compounds." In instances where changes in expression levels when the cells are contacted with the test compound are identical (or at least similar) to changes in expression levels when the cell are contacted with the known therapeutic compound, then the test compound is identified as a "drug candidate" compound for treating the CNS disorder. Thus, using these screening methods a skilled artisan is able to rapidly and inexpensively identify compounds that are most promising as novel drugs for treating CNS disorders, while eliminating compounds that show little promise and/or are unlikely candidates for this purpose.

In addition, the "drug-candidate signature" may also be compared to the "disease signature". Preferred drug candidates are those which alters the expression of "signature gene" in a way that is opposite or contrary to the expression observed in the disorder's gene signature. For example, where a particular gene is expressed at abnormally high levels in cells or tissues from individuals affected by the particular CNS disorder (compared to expression levels in cells or tissues from individuals not affected by the disorder), a candidate compound identified in these screening methods will preferably inhibit that gene's expression (i.e., the gene is preferably expressed at lower levels when the cells are contacted with the test compound, compared to its expression when the cell is not contacted with the test compound).

Differentiation Assays. In one particular embodiment, the screening assays is designed to screen for compounds that affect 5HT1A-induced differentiation of neural stem cells. The assay can, for example, be based on genes that are specifically expressed in differentiating neural stem cells, and identify compounds which affect the expression of these genes. Alternatively, the assays can identify phenotypic changes in differentiating cells such as the expression of antigens typical of specific types of cells (see above). In a specific embodiment, the method can identify a compound that affects differentiation of mammalian neural stem cells by (a) exposing a first population of cultured multipotent or pluripotent neural stem cells to a 5HT 1A agonist in an amount sufficient to induce differentiation of said cells preferentially into neurons in the presence of a test compound, (b) exposing a second population of multipotent or pluripotent neural stem cells to the same amount of 5H1A agonist in the absence of the test compound, which test compound can be added before or after the 5HT1A agonist, and comparing the portion of neurons resulting in step (a) to the portion of neurons resulting in step (b). If a difference is found, the test compound affects neuronal differentiation and is a "lead compound."

Any screening technique known in the art can be used to screen for compounds that modulate 5HT1A agonist-induced neuronal differentiation, including gene expression techniques. The present invention contemplates screens for synthetic small molecules as well as screens for natural molecules that agonize or antagonize the activity of differentiation in vivo. For example, natural products libraries can be screened using assays of the invention for molecules that agonize or antagonize plasma cell activity.

Gene Expression Evaluation. Gene expression evaluation technologies, such as differential display and subtractive hybridization methods, can be used in the present invention to ascertain genes that are expressed or turned off in differentiated or differentiating neural stem cells, such as subtractive hybridization (see, e.g., U.S. Pat. No. 5,700,644, issued to Gould et al. and U.S. Pat. No. 5,665,547, issued to Pardee et al.). In addition, oligonucleotide expression array technology can be used to evaluate gene expression, and to identify gene expression that either correlates with or is distinct from gene expression in diseased neurons (see, e.g., Little et al., Genet. Anal. 6:151, 1996).

By way of example, GeneChip expression analysis (Affymetrix, Santa Clara, Calif.) generates data for the assessment of gene expression profiles and other biological assays. Oligonucleotide expression arrays simultaneously and quantitatively interrogate thousands of mRNA transcripts (genes or ESTs), simplifying large genomic studies. Each transcript can be represented on a probe array by multiple probe pairs to differentiate among closely related members of gene families. Each probe cell contains millions of copies of a specific oligonucleotide probe, permitting the accurate and sensitive detection of low-intensity mRNA hybridization patterns. After hybridization intensity data is captured, e.g., using a Hewlett-Packard GeneArray™ scanner, software can be used to automatically calculate intensity values for each probe cell. Probe cell intensities can be used to calculate an average intensity for each gene, which directly correlates with mRNA abundance levels. Expression data can be quickly sorted on any analysis parameter and displayed in a variety of graphical formats for any selected subset of genes. Other gene expression detection technologies include the research products manufactured and sold by Perkin-Elmer and Gene Logic.

Test compounds. As used herein, the term "test compound" refers to any protein or polypeptide, nucleic acid (such as an antigens or ribosome nucleic acid), or small molecule compound, including steroid hormone, arachidonic acid metabolite (leukotriene or prostaglandin), small peptide hormone (e.g., an opioid), or synthetic organic molecule.

Antigens nucleic acids (including ribozymes), may be used to inhibit expression of one or more specific proteins in order to modulate neuronal differentiation. Such antigens nucleic acids can be tested using the present invention for in vivo activity. An "antigens nucleic acid" is a single stranded nucleic acid molecule which, on hybridizing under cytoplasmic conditions with complementary bases in an RNA or DNA molecule, inhibits the latter's role. If the RNA is a messenger RNA transcript, the antigens nucleic acid is a counter transcript or mRNA-interfering complementary nucleic acid. As presently used, "antigens" broadly includes RNA-RNA interactions, RNA-DNA interactions, ribozymes and RNase-H mediated arrest. Antigens nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607).

Classes of compounds that may be identified by such screening assays include, but are not limited to, small molecules (e.g., organic or inorganic molecules or peptides which are less than about 2 kD in molecular weight, are more preferably less than about 1 kD in molecular weight, and/or are able to cross the blood-brain barrier or gain entry into an appropriate cell, as well as macromolecules (e.g., molecules greater than about 2 kD in molecular weight). Compounds identified by these screening assays may also include peptides and polypeptides. For example, soluble peptides, fusion peptides members of combinatorial libraries (such as ones described by Lam et al., Nature 1991, 354: 82–84; and by Houghten et al., Nature 1991, 354:84–86); members of libraries derived by combinatorial chemistry, such as molecular libraries of D- and/or L-configuration amino acids; phosphopeptides, such as members of random or partially degenerate, directed phosphopeptide libraries (see, e.g., Songyang et al., Cell 1993, 72:767–778); antibodies, including but not limited to polyclonal, monoclonal, humanized, anti-idiotypic, chimeric, or single chain antibodies; antibody fragments, including but not limited to FAb, F(ab')2, FAb expression library fragments and epitope-binding fragments thereof.

One approach uses recombinant bacteriophage to produce large libraries. Using the "phage method" (Scott and Smith, Science 249:386–390, 1990; Cwirla, et al., PNAS USA 87:6378, 1990; Devlin et al., Science, 49:404, 1990), very large libraries can be constructed (106–108 chemical entities). A second approach uses primarily chemical methods, of which the Geysen method (Geysen et al., Molecular Immunology 23:709, 1986; Geysen et al. J. Immunologic Method 102:259, 1987; and the method of Fodor et al. (Science 251:767, 1991) are examples. Furka et al. (14th International Congress of Biochemistry, Volume #5, Abstract FR:013, 1988; Furka, Int. J. Peptide Protein Res. 37:487–493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., Proc. Natl. Acad. Sci. USA 90:10700–4, 1993; Ohlmeyer et al., PNAS USA 90:10922, 1993; Lam et al., International Patent Publication No. WO 92/00252; Kocis et al., International Patent Publication No. WO 9428028) and the like can be screened for molecules that have CNS or PNS activity restorative of abnormal expression of genes within a gene signature.

The compounds used in such screening assays are also preferably essential pure and free of contaminants that may, themselves, alter or influence gene expression. Compound purity may be assessed by any number of means that are routine in the art, such as LC☐MS and NMR spectroscopy. Libraries of test compounds are also preferably biased by using computational selection methods that are routine in the art. Tools for such computational selection, such as Pipeline Pilot™ (Scitegic Inc., San Diego, Calif.) are commercially available. The compounds may be assessed using rules such as the "Lipinski criteria" (see, Lipinski et al., Adv. Drug Deliv. Rev. 2001, 46:3–26) and/or an other criteria or metrics commonly used in the art.

In summary, the method of the invention can be applied for large scale preparations of complex systems (including neurons) for the screening of compounds in high-throughput screens for drug candidates and for gene discovery purposes. As discussed above, the generation of primary neuronal cultures from human central nervous system has been problematic because of the limited availability of post-mortem, and even less of live tissue, from which to make such cultures. Thus, the present invention provides an alternative method by which these cultures may be generated. Neural stem cells are a better source of primary human cultures than post-mortem tissues or live tissues, because they are capable of dividing in culture, and can be applied as a renewable resource from which neurons and neuronal systems may be generated using 5HT1A agonists.

Treatment of CNS or PNS Disorders

Nervous system disorders such as neurodegenerative diseases have a major impact on society. For example, approximately 3 to 4 million Americans are afflicted with the chronic neurodegenerative disease known as Alzheimer's disease. Other examples of chronic neurodegenerative diseases include diabetic peripheral neuropathy, multiple sclerosis, amyotrophic lateral sclerosis, Huntington's disease and Parkinson's disease. Not all neurodegenerative diseases are chronic. Some acute neurodegenerative diseases include stroke, schizophrenia, and epilepsy as well as hypoglycemia and trauma resulting in injury of the brain, peripheral nerves or spinal cord. There is a need for improved therapeutic agents and methods for reversing and retarding neuronal damage associated with each of these conditions, or promoting neuronal generation.

A common feature of neurodegenerative disorders and the process of aging in animals is the progressive cell damage of neurons within the central nervous system (CNS) or peripheral nervous system (PNS) leading to loss of neuronal activity and cell death. This loss of activity has been correlated with adverse behavioral symptoms including memory loss and cognitive deficits. Therapeutic agents that have been developed to retard loss of neuronal activity either have toxic side effects or are prevented from reaching their target site because of their inability to cross the blood-brain barrier. The blood-brain barrier is a complex of morphological and enzymatic components that retards the passage of both large and charged small molecules thereby limiting access to cells of the brain. There is thus a need for novel therapeutic agents that are readily transported across the blood-brain barrier as well as for novel methods of treatment of neurodegenerative disorders that directly target the damaged site and are non-toxic.

It is now recognized that neuronal cell density has an important impact on function. In various pathological conditions, loss of cell density has been observed resulting from accelerated neuronal cell death. The pattern of degeneration of neurons typically originates from the nerve terminals and progresses "backward" toward the cell body (retrograde degeneration). In several systems, lesioning of certain brain regions results in compensatory sprouting of axons. This plasticity of neurons is attributed at least in part to the presence of trophic growth factors. At present, however, there is no treatment for neurodegenerative disease which effectively prevents, retards, or turns around the progressive neurodegeneration of the brain and cognitive decline associated with the illness.

In animal models and cell cultures, neurotrophic and neuritogenic factors such as nerve growth factor (NGF) and gangliosides, have demonstrated initial therapeutic effects, which indicates that these substances may be of benefit to patients afflicted with Alzheimer's disease. See Frey, W. H., II and T. A. Ala, Progress in Clinical Neuroscience 1:287–303 (1988), and Seiler, Brain Res. 300:33–39 (1984). Potentially, therapeutic agents could be identified that compensate for cell loss by stimulating sprouting of dendrites and axons of remaining cells so as to improve the structural integrity of the damaged region.

Alternatively, treatment of neurological disorders, such as neurodegenerative diseases and neurotrauma, has focused on replacing damaged neural cells with healthy cells. U.S.

Pat. No. 5,762,926 to Gage et al., and U.S. Pat. No. 6,395,546 to Zobel et al. hereby incorporated herein by reference, describe neuronal transplantation. Such strategies could be used to replace the injured or depleted neural cells with new neural cells, thus potentially providing treatment of spinal cord injuries and progressive neurodegenerative disorders such as Alzheimer's disease, Parkinson's disease, Huntington's disease, amyotrophic lateral sclerosis and hereditary ataxia as well as to study other diseases, conditions and disorders characterized by loss, damage or dysfunction of neurons including transplantation of neuron cells into individuals to treat individuals suspected of suffering from such diseases, conditions and disorders. Recent studies utilizing human fetal mesencephalic tissue grafts to ameliorate the extrapyramidal manifestations of drug induced and idiopathic Parkinson's disease emphasize the potential of transplanted human CNS tissues for the treatment of human neurodegenerative diseases (Freed, C. A., et al. 1992 New Engl. J. Med. 327:1549–1555; Spencer, D. D. et al. 1992 New Engl. J. Med. 327:1541–1548; and Widner, H., et al. 1992 New Engl. J. Med. 327:1556–1563). However, major obstacles in the field of neuronal transplantation is the inadequacy of donor material, the inability in the prior art of the transplant to fully integrate into the host tissue, and the lack of availability of cells in unlimited amounts from a reliable source for grafting. Since adult neural tissue undergoes minimal division, it does not readily meet these criteria. While in recent years, therapeutic transplantations have been performed using human fetal tissue as the donor substrate, this is a controversial ethical dilemma which is also hampered by critical methodological difficulties. A renewable source of normal human neural cells would be an indispensable tool in clinical studies of neurotrauma and neurodegenerative diseases.

Accordingly, the findings of the present invention can be used for (a) stimulating the differentiation of neurons from adult stem cells in vivo, or (b) providing a source of cells for neural transplantation.

Stimulating neural differentiation in vivo. As described herein, 5HT1 agonists can be used to promote the differentiation of neural stem cells into neurons. Thus, compounds that are determined to have 5HT1A agonist activity may be administered (e.g., to an individual suffering from a CNS disorder) at therapeutically effective doses to enhance neuronal differentiation in vivo. A "therapeutically effective dose" is an amount of the compound that is sufficient to result in enhanced differentiation of neural stem cells into neurons.

Toxicity and therapeutic efficacy of the 5HT1A agonists can be determined by standard pharmaceutical procedures, for example in cell culture assays or using experimental animals to determine the LD50 and the ED50. The parameters LD50 and ED50 are well known in the art, and refer to doses of a compound that are lethal to 50% of a population and therapeutically effective in 50% of a population, respectively. The dose ratio between toxic and therapeutic effects is referred to as the therapeutic index and may be expressed as the ratio: LD50/ED50. Compounds that exhibit large therapeutic indices are preferred. While compounds that exhibit toxic side effects may be used. However, in such instances it is particularly preferable to use delivery systems that specifically target such compounds to the site of affected tissue so as to minimize potential damage to other cells, tissues or organs and to reduce side effects.

Data obtained from cell culture assay or animal studies may be used to formulate a range of dosages for use in humans. The dosage of compounds used in therapeutic methods of the present invention preferably lie within a range of circulating concentrations that includes the ED50 concentration but with little or no toxicity (e.g., below the LD50 concentration). The particular dosage used in any application may vary within this range, depending upon factors such as the particular dosage form employed, the route of administration utilized, the conditions of the individual (e.g., patient), and so forth.

A therapeutically effective dose may be initially estimated from cell culture assays and formulated in animal models to achieve a circulating concentration range that includes the IC50. The IC50 concentration of a compound is the concentration that achieves a half maximal inhibition of symptoms (e.g., as determined from the cell culture assays). Appropriate dosages for use in a particular individual, for example in human patients, may then be more accurately determined using such information. Alternatively, amounts administered to patients for other purposes, e.g., in the case of buspirone, to treat depression, can be tested for their safety and efficacy in treating CNS disorders characterized by neuronal damage or depletion of.

Pharmaceutical compositions for use in accordance with the present invention may be formulated in conventional manner using one or more physiologically acceptable carriers or excipients. Thus, the compounds and their physiologically acceptable salts and solvates may be formulated for administration by inhalation or insufflation (either through the mouth or the nose) or oral or parenteral administration. For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p hydroxybenzoates or sorbic acid). The preparations may also contain buffer salts, flavoring, coloring and sweetening agents as appropriate.

Preparations for oral administration may be suitably formulated to give controlled release of the active compound. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use. The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

Neural transplantation. The differentiated neurons or differentiating neural stem cells produced by the method of the present invention may be used to treat individuals suffering from injuries, diseases, conditions or disorders characterized by the loss, damage or dysfunction of endogenous cells. Transplantation of the differentiated neurons or differentiating neural stem cells neurons may be used to treat individuals suffering from stroke, spinal injury or other injuries, conditions or disorders associated with neuron damage or death. CNS diseases and disorders which may be treated include any disease of the CNS which is characterized by the loss, damage or dysfunction of endogenous cells, the symptoms of which may be reversed or reduced in severity by providing neurons that can replace such cells and produce products needed for proper function or needed to counteract the presence of compounds that are not normally present or present at abnormal levels. The present invention is useful for the treatment of progressive neurodegenerative disorders such as Alzheimer's disease, Parkinson's disease, Huntington's disease, amyotrophic lateral sclerosis and hereditary ataxia, as well as neurological conditions such as strokes and nerve injuries. The multipotent neural stem cell progeny can be continuously passaged and proliferation reinitiated in the presence of a 5HT1A agonist to result in an unlimited supply of neural cells for neurotransplantation and other purposes.

In a further embodiment, the neural stem cells obtained using the method of the present invention can be manipulated to express desired gene products. The proliferating neural cells can be transfected with exogenous DNA to produce genetically modified neural stem cell progeny. Alternatively, the neural stem cells can be transfected prior to differentiation according to the invention. The genetic modification can be for the production of biologically useful proteins such as growth factor products, growth factor receptors, neurotransmitters, neurotransmitter receptors, neuropeptides and neurotransmitter synthesizing genes.

Neurons may be implanted into the brain, spinal cord, or at or near the site of nerve damage from disease or injury. Neurons of the invention are implanted at the site of the nerve cell injury, i.e., in proximity to the injured cell or cells at a location where the implanted cells can replace nerve function and/or reconnect nerves of the individual to remedy or otherwise ameliorate the injury or disorder.

The transplanting of cultured cells of the invention into the brain of an animal, including a human, is a relatively simple process. A tube of appropriate diameter is inserted to the desired region of the brain, e.g., the striata, and a suspension of cells in a physiologically acceptable carrier is allowed to flow through the tube into the brain at a controlled rate, to the desired location. A physiologically acceptable carrier can be any sort of solution having non-toxic, non-injurious components for either the cells or the tissue at the site of transplant. Typically, a physiologically acceptable carrier will include a solution of salts compatible with live cells and tissue having pH, osmolarity and chemical composition ranges known in the art, for example, Hank's buffer.

Presently, one main technique or a variation thereof is used for transplanting neural tissue. See e.g., Kordower, J. H. et al. (1995) N. Engl. J. Med. 332(17):1118–1124; Freeman, T. et al. (1995) Annals Neurol. 38(3):379–388; Widner, H. et al. (1992) N. Engl. J. Med. 327(22):1556–1563. This technique employs a cell or tissue delivery device which includes a stereotaxic needle with a blunt end and a tip diameter from about 0.9 to about 1.5 mm. The cells or tissue to be transplanted are loaded into this needle, the needle is advanced toward the transplant site, and the cells or tissue are released from the needle at the site. Using this needle, multiple grafts can be placed along a straight path. However, if one wishes to graft at a site which is not along this path, the needle must be removed and reinserted along a new path. Reinsertion of this needle causes additional trauma to the tissue in the path of the needle. Typically, it is desirable to make multiple grafts along different paths. In such a case, the needle is generally removed and reinserted into the subject from about six to about eight times per side of the brain, increasing trauma to the brain tissues with each new penetration.

In addition to the simple injection needles described above, other instruments have been described for transplantation of tissue into the brain. See U.S. Pat. Nos. 5,006,122 and 5,004,457. U.S. Pat. No. 5,006,122 discloses a brain tissue transplantation method utilizing a cannula within a cannula assembly. The first cannula is a large bore cannula which is fixed to a stereotaxic holding apparatus and which is advanced into the brain to the transplant site. The second cannula, which carries donor tissue and a stylet which is used to expel the tissue from the second cannula, is guided within the lumen of the first cannula to the transplant site. The tissue is then transplanted into the brain by withdrawing the first and second cannulas while the stylet within the second cannula is maintained in a fixed position. The stylet is later removed, leaving only the transplanted tissue in the recipient.

In addition, U.S. Pat. No. 5,792,110 describes a system for delivering therapeutic agents, including cells, to a selected site in a subject, including the brain, to a predetermined depth using a delivery cannula for delivering the therapeutic agent to the subject. The guide cannula has an axial bore extending therethrough with an open proximal end and an opening at a distal portion thereof. The delivery cannula has an axial bore extending therethrough, a flexible distal end portion, and an outer diameter which is less than the inner diameter of the guide cannula.

In summary, the capacity to efficiently differentiate neurons as opposed to protect mature neurons from injury or degeneration is important both for the treatment of neurodegenerative diseases and in vitro studies of cells to be used in transplantation, or to be used for research and drug screening processes.

EXAMPLES

Examples of practicing the invention are provided, and are understood to be exemplary only, and do not limit the scope of the invention or the appended claims. A person of ordinary skill in the art will appreciate that the invention can be practiced in many forms according to the claims and disclosures here.

Example 1

Differentiation of Neural Stem Cells into Neurons 5HT1A Agonists

This Example describes the differentiation of cortical, cerebellar and striatal neural stem cells obtained from rat embryos. Stem cell differentiation was initiated by treatment with buspirone and serotonin, which bind to and signal through 5TH1A receptors, and the amount of neurons obtained after treatment estimated by staining with an anti-β-tubulin antibody (TuJ-1). Neuronal differentiation of neural stem cells using buspirone in combination with BDNF was also investigated. Untreated cells, or cells treated with bFGF with or without buspirone, were used as controls. As can be seen from the results, buspirone effectively differentiates neural stem cells into neurons; BDNF is not necessary for the buspirone effect; and the presence of bFGF inhibits buspirone-mediated differentiation. The effect induced by combining BDNF with buspirone is of interest since the mechanism for differentiation may differ from that when using buspirone alone. Similar to results observed with buspirone, serotonin, the natural ligand for the 5HT1A receptor, also accelerated the differentiation of neural stem cells into neurons. Both buspirone- and serotonin-induced differentiation could be inhibited by a 5HT1A antagonist, demonstrating that the differentiation is mediated through the 5HT1A receptor.

Methods

Isolation and quantitation of cerebellar stem cells. Neural stem cells were isolated from rat embryos (obtained from Taconic) at the 19th day of gestation (E19). The rats were sacrificed by inhalation of excess carbon dioxide. The abdomen of the rat was cleaned with 70% ethanol and the uterus was removed quickly and aseptically on the bench top. The uterus was placed in ice cold PBS (GIBCO Cat. # 20012-027) in a 200-ml beaker.

Embryos were removed from the uterus, rinsed in PBS and collected in cold HBSS (buffered with HEPES and sodium bicarbonate-see below) in a 200-ml beaker and placed on ice. All operations were performed on ice (or cold buffers on the bench top). All procedures leading to the collection of tissue should be performed with maximum speed, as this results in improved viability of cultures.

HBSS solution:

100 ml   10X Ca2+/Mg2+ free HBSS (GIBCO Cat. # 12500-039)
3.7 gm   NaHCO3 (SIGMA Cat. # S-5761)

-continued 3.9 gm   HEPES (SIGMA Cat. # H-3784)
800 ml   ddH2O

The above mixture is dissolved in HBSS and the pH adjusted to 7.2 with 1N HCl. The final volume is made up to 1000 ml with ddH20. The solution is filtered and stored at 4° C.

The cerebellar tissue was dissected under a microscope according to the following procedure and collected in a 15-ml tube containing HBSS on ice. The dissection should be completed in 1–2 hours (optimally) and the pH of the HBSS should remain neutral. First, the neck of the embryos was severed towards the bottom and the heads were collected in cold PBS. Next, the skin and scalp was removed from neck and head of the embryo. The brain, including the cerebral cortex, midbrain, cerebellum and some of the spinal cord, was removed by dissection under a microscope and transfered into a clean dish with fresh, cold PBS. The cerebellar region was dissected and cleaned of extraneous tissue, including removal of the meninges, and transferred into cold HBSS in a clean 15 ml tube.

Following the dissection, the 15-ml tube containing the relevant tissue is sprayed with 70% ethanol and taken into the hood. All the subsequent steps are performed under sterile conditions in a bio-safety cabinet.

The tube containing the cerebellar tissue was centrifuged at 1,000 RPM for 2 min at 15 C., followed by slow, careful aspiration of the HBSS supernatant (care should be taken to avoid aspirating tissue). (It is best to limit the centrifugation steps as much as possible.) About 1 to 3 ml of DMEM/F12/N2 medium (see below) was immediately added to the remaining tissue; the volume of medium depends on the quantity of the dissected tissue. The tissue was gently triturated about 8 to 10 times using a P-1000 Pipetteman until the tissue was dissociated (as evidenced by cloudy solution), then the tube was incubated in the hood for 5 minutes at room temperature to permit settlement of small particles of undissociated tissue. The supernatant was then transferred into a fresh tube, taking care to avoid the smaller particles of tissue that remained at the bottom of the tube.

Cells were counted twice under microscope by using a hemocytometer. For counting, a 1:10 dilution ratio of the cell solution: trypan blue solution (Gibco, Cat #15250-061) was used, and numbers of cells that excluded the dye were averaged from 2–4 quadrants of the hemocytometer. The resulting figure was then multiplied by the dilution factor (10). The volume enclosed in one quadrant of a hemocytometer was calibrated to be 0.0001 ml. The number of cells present in 1 ml of the cell suspension was determined.

Preparation of culture medium and tissue culture dishes. Prior to plating of isolated cells, 10 cm culture dishes (Falcon) were incubated at 37° C. overnight with 5 ml of 1.5 mg/ml poly-ornithine (Sigma Cat #P-3655) dissolved in water. Following overnight incubation, the dishes were washed twice with ddH$_2$O, coated with 5 ml of 1 mg/ml fibronectin (Invitrogen Cat #33010-018) in PBS, and incubated overnight. Following incubation, the culture dishes were washed once with PBS, filled with PBS, and stored in the incubator until use. The coated dishes should not be stored at 37° C. for more than 10 days.

Growth medium was prepared according to the following:

DMEM/F12 medium:

| | |
|---|---|
| 1 pack | DMEM-F12 powder (GIBCO Cat. # 12500-039) |
| 1.55 g | D-(+)-Glucose (SIGMA Cat. # G-8270) |
| 1.69 g | NaHCO3 (SIGMA Cat. # S-5761) |
| 73 mg | L-Glutamine (SIGMA Cat. # G-5763) |
| 800 ml | ddH$_2$O |

The above-listed reagents were mixed using a magnetic stir bar until completely dissolved. The pH was to 7.2 by the addition of 1N HCl as assessed using a pH meter.

DMEM/F12/N2 (1000 ml volume):

The following reagents were added to about 630 ml of the above medium:

| | |
|---|---|
| 100 µl | 1M Putrescine (SIGMA Cat. # P-5780) |
| 60 µl | 0.5 mM Sodium selenite (SIGMA Cat. # S-5261) |
| 200 µl | 0.1 mM Progesterone dissolved in EtOH (SIGMA Cat. # P-8783) |
| 100 mg | Human apo-transferrin (SIGMA Cat. # T-2036) |
| 10 ml | 100 × Penicillin-Streptomycin (GIBCO Cat. # 15070-063) |

Added to the medium immediately prior to use:

| | |
|---|---|
| Insulin | (INTERGEN Cat. # 4501-01) at 25 mg/L |
| 10 ng/ml recombinant human basic fibroblast growth factor (bFGF, R&D Systems) | |

Following addition of N2, the growth medium was sterile filtered and stored at 4° C. This medium should not be used after storage for longer than 2 weeks.

Plating and expansion of cerebellar stem cells. The triturated cell suspension of E19 rat cerebellum was seeded into pre-coated 10 cm dishes at $2\times10^6$ cells per dish. This is denoted as the P0 culture (passage 0). The cells were grown in 5 ml of DMEM/F12/N2 supplemented with 25 mg/L insulin and 10 ng/ml bFGF at 37 C, 5% $CO_2$ and 90% humidity.

Cells were fed daily with 10 ng/ml bFGF. The medium was changed one day after the cells were seeded, and thereafter every other day. On about day 4 of the culture, or when cells reached 70% confluence, the culture was passaged (see "Passage of cerebellar stem cells" below) and seeded into 10 cm dishes at an initial density of $2\times10^6$ cells per dish. This is denoted as the P1 culture (passage 1). The passaged cells at P1 were grown in DMEM/F12/N2 medium supplemented with 25 mg/L insulin and 10 ng/ml bFGF. The medium was changed every other day.

After two days of culture, some cells were passaged into a P2 culture, and some were seeded in 12-well tissue culture plates for experimental use. One ml of DMEM/F12/N2 medium was used per well of a 12-well plate at $2\times10^4$ cells per well. Experimental treatments were initiated the day after passage.

Passage of cerebellar stem cells. Medium was aspirated from the dishes and rinsed twice with HBSS. Cells in each dish were incubated in 7 ml of 1× HBSS buffer at 37° C. for about 20 minutes. During the incubation, dishes were grossly examined periodically to estimate the percentage of cells that rounded up.

Following the incubation, the HBSS medium was pipetted 3–4 times with a 10 ml pipette to gently dislodge the cells from the dish. Cells were collected into a sterile 50 ml centrifuge tube and centrifuge 2 minutes at 1,000 g and 15 C. with no brake on the rotor. The supernatant was then carefully aspirated to avoid loss of cells, and the cells were re-suspended in 2 ml of DMEM/F12/N2 medium containing 25 mg/L insulin and 10 ng/ml bFGF. Cells were counted and plated as described supra. It is preferable that handling or establishment of the 'master cultures' is done by one designated person to ensure consistent reproducibility, Isolation of cortical and striatal stem cells. Timed pregnant Sprague Dawley rats obtained from Taconic at embryonic age E14-E15 were sacrificed as described above and the uterus removed and placed in ice cold PBS in a 10 cm petridish. After rinsing the uterus in PBS, embryos were removed from the uterus, rinsed in PBS and collected in cold HBSS (buffered with HEPES and sodium bicarbonate) in a 10 cm petridish and placed on ice.

The cortex and striatum was dissected under a microscope and collected in a 15 ml tube of HBSS, on ice. Removal of meninges is not possible at this age, and no attempt was made to do so. If the dissected tissue was in large enough chunks and settle to the bottom of the tube, no centrifugation was performed. Alternatively, the tube was centrifuged at 1000 rpm for 5 minutes to pellet the tissue. Following centrifugation, the 15 ml tube containing the tissue was sprayed with 70% ethanol and taken into the sterile hood.

The HBSS was aspirated and replaced with 10 ml of DMEM/F12. The tissue was collected at the bottom of the tube by gravity or centrifugation, medium was aspirated, and 1 ml of DMEM/F12 was to the tissue. Cells were dissociated by trituration as described above, followed by addition of 5 ml of DMEM/F12 and a second round of trituration. There remained smaller chunks of tissue in the tube after dissociation, along with 'sheets' of meninges. The tubes were placed standing 5–10 minutes in the hood to allow larger particles and meninges to settle. While the meninges were settling, a cell count was made. 10 µl of the cell suspension is diluted with trypan blue and counted in a hemocytometer. Cells were counted in the four outer chambers with the larger squares, and cell count calculated assuming that the volume enclosed in each of the chambers was 0.1 ml.

Plating, expansion and passaging of cortical and striatal stem cells A generous amount of the triturated cell suspension was left in the original 15 ml tube to avoid fibroblast contamination in cultures. About 4–5 ml of the 6 ml of cells suspension was used for plating. Cells were plated at a concentration of approximately $1\times10^6$ per 10 cm dish. This culture is designated P0 (passage 0).

Following plating cells were expanded for about 3–4 days. The cultures were never permitted to reach more than 70% confluency. Cultures were then passaged as follows: 5 ml of HBSS was added to each 10 cm dish and the cells incubated at 37° C. for 15–45 minutes, or until sufficient numbers of the stem cells were rounded up. It is not expected that all cells in the culture will round up as there are several cell types in the culture at P0. The pH of the HBSS should be neutral at all times during this incubation. Cells were then removed from the dish by pipetting with a 5 ml pipette, or by scraping with a policeman, collected in a 15 or 50 ml conical tube, and centrifuged at 1000 g for 5 minutes. Cells were gently re-suspended in medium, counted, and plated at a density of about $1\times10^6$ per 10 cm dish.

Drug treatments. Stem cells obtained as described above were treated with drugs and subjected to differentiation protocols in the second passage. Cells were plated at a density of $1\times10^4$ cells per well of a 12-well petridish (Falcon). They were plated in DMEM/F12/N2 medium that did not contain bFGF.

Drug treatments were started on the next day. Optimal concentrations were as follows: bFGF: 10 ng/ml; BDNF (R&D Systems, Minneapolis, Minn.): 20 ng/ml; buspirone (Sigma): 100–1000 nM; or Serotonin (Sigma): 5–10 μM; buspirone or serotonin and the 5HT1A antagonist WAY100635 (Sigma): 10 nM. The WAY 100635 antagonist compound was used simultaneously with buspirone or serotonin in the blocking experiments. Positive and negative control cultures were those treated with BDNF and FGF alone, respectively.

Cells were treated with the designated concentrations of drugs or combinations thereof, daily, and were fed every alternate day with fresh medium. Experiments were maintained for about 6–10 days in most cases. Cells were fixed on about day 7–11 with a 4% solution of para-formaldehyde (PFA) in PBS, prepared as follows:

PFA:

4 g of paraformaldyde.

4.1 g of sucrose 80 ml of PBS

The solution was heated to approximately 70–80° C. for about 2–3 hours under a safe chemical hood while stirring to medium speed. Solution was not allowed to boil. Once the solution became clear, the pH was measured using pH paper and adjusted with sodium hydroxide to about. 7.2. The volume was adjusted to 100 ml and filtered. Solutions older than 1 week should not be used.

For fixing, the medium was aspirated from the cell culture dishes, and cells were exposed to 1–10 ml as required ice cold PFA for 15–20 minutes at room temperature. Cells were then washed twice with cold PBS for 15 minutes each.

Immunofluorescent staining and visualization. After fixation, the PBS was aspirated from the fixed cells and the cells were treated with blocking solution (10% normal goat serum-NGS-Jackson Labs), 0.3% Triton-Sigma, in PBS) to saturate non-specific sites and permeabilize the cells. Following blocking, cells were incubated with the following designated primary antibodies diluted in 5% NGS for 1 hour at room temperatuare: mouse monoclonal anti-MAP-2 (Sigma): 1/250 dilution; mouse monoclonal anti-β tubulin III (Covance): 1/600 dilution; mouse anti-monoclonal glial fibrillary acidic protein (GFAP-ICN Biomedicals): 1/100 dilution.

After the 1 hour incubation, cells were washed three times for 5 min each with PBS followed by incubation of a goat anti-mouse secondary antibody conjugated with stains Cy2 and Cy3 (Jackson Labs) for 1 hr at RT (dilution 1/100 as with the primary antibodies). Following three 5 minute washes with PBS, cells were incubated with the nuclear stain bis-benzimide (Sigma) for 10 min at RT. Cells were then washed 3 times with ultra-pure water and glass coverslips were mounted on them using AquaPolymount (Polysciences, Inc., PA) The mount was allowed to dry and the dishes were stored at 4° C.

For visualization of staining, the mounted cells were viewed under a fluorescent microscope using the appropriate ultra violet filters. An eyepiece with an engraved grid was used to count the cells that stained positive for β tubulin III (TuJ-1), MAP2 or GFAP. The percent of cells positive for a given antigen was estimated by counting nuclei of all cells present in the same field, as the nuclei of the cells stain blue with the bis benzimide. Five fields were counted per treatment condition, and averages with standard deviations were calculated.

Results

Buspirone induces neuronal differentiation of neural stem cells. Initial experiments were performed in which buspirone was compared with mitogenic growth factor bFGF and BDNF to assess differentiation of neural stem cells isolated from the cortex of E19 rat embryos. Cells were expanded for 5 days in growth medium containing 10 ng/ml bFGF, and then placed in medium containing bFGF, BDNF, 1 μM buspirone, bFGF plus buspirone, or BDNF plus buspirone and treated for 6 days. Neuronal differentiation was assessed by immunofluorescence using an antibody specific for βtubulin III. (TuJ-1). Results are shown in Tables 1 and 2 below.

As shown in Table 1, cells maintained in medium containing only the mitogenic growth factor bFGF, or bFGF in combination with 0.1 μM or 1 μM buspirone, did not differentiate into neurons, as evidenced by lack of fluorescent staining for β tubulin III. By contrast, neural stem cells treated with BDNF alone, a known neuronal differentiation factor, exhibited some neuronal differentiation (about 6%). The proportion of cells differentiating with BDNF was significantly enhanced in a dose-dependent manner by the addition of either 0.1 μM or 1 μM buspirone. Surprisingly, cells treated with 1 μM buspirone alone demonstrated significant neuronal differentiation, similar to the combination of buspirone and BDNF, and demonstrated superior neuronal differentiation than when treated with BDNF alone. These results indicate that buspirone is the responsible for the accelerated differentiation observed in the cultures treated with a combination of buspirone and BDNF.

TABLE 1

Neuronal differentiation of cortical neural stem cells using Buspirone and/or BDNF

| Treatment | No. Fluorescent Cells | Total No. of Cells | % Fluorescent Cells | Standard Deviation |
|---|---|---|---|---|
| 1. 10 ng/ml bFGF | 33 | 7330 | 0.48 | 0.27 |
|  | 65 | 10210 | 0.63 | 0.29 |
| 2. bFGF + 0.1 μM Buspirone | 58 | 8130 | 0.71 | 0.21 |
|  | 70 | 9000 | 0.79 | 0.21 |
| 3. bFGF + 1 μM Buspirone | 44 | 7220 | 0.65 | 0.40 |
|  | 82 | 9720 | 0.86 | 0.26 |
| 4. 20 ng/ml BDNF | 38 | 624 | 6.38 | 3.80 |
|  | 308 | 1006 | 30.49 | 7.48 |
| 5. BDNF + 0.1 μM Buspirone | 203 | 1070 | 18.85 | 6.11 |
|  | 308 | 1006 | 30.49 | 7.48 |
| 6. BDNF + 1 μM Buspirone, | 351 | 1262 | 27.88 | 5.74 |
|  | 403 | 1407 | 28.86 | 4.83 |
| 7. 1 μM Buspirone | 320 | 1168 | 27.27 | 5.21 |
|  | 260 | 1228 | 20.15 | 7.03 |

Figure 3A:
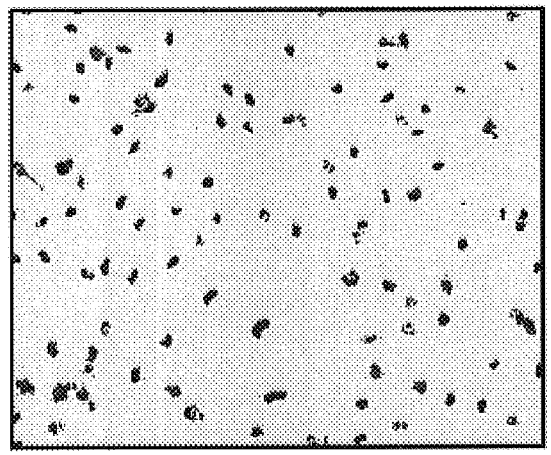
FIGS. 3A–B show immunostaining of rat cerebellar stem cells treated with either a solvent (FIG. 3A) or 100 nM buspirone (FIG. 3B). Neuronal differentiation is estimated by cells which stain red (TuJ1), while total cell number is determined by counting the bis-benzamide-stained nuclei (blue). The bar in FIG. 3B represents 100 microns.
Figure 3B:
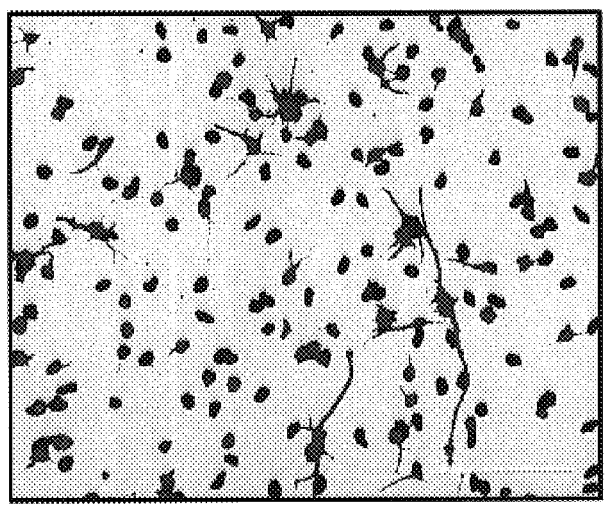

FIG. 1 and Tables 2–5 show results from experiments evaluating a dose-response of various buspirone concentrations on the differentiation of cerebellar neural stem cells. The results in FIG. 1 demonstrate that a dosage range of between 10 nM to 300 nM is effective to induce neuronal differentiation of about 40–55% of neural stem cells (FIG. 1, lanes 2–5), with the highest percentage being induced at a concentration of about 0.1 M (100 nM) of buspirone (lane 4). The results from Tables 2–5 (which represent separate experiments) demonstrate that concentrations of buspirone from 10 nm to 100 um are effective at promoting neuronal differentiation of neural stem cells. The photographs in FIG. 3 represent results from immunostaining the rat cereballar cultures treated with either solvent (FIG. 3A) or buspirone (100 nM-FIG. 3B). The red color demonstrates positive staining for the neuronal marker TuJ1, while the blue stain represents the total number of cells in the culture as indicated by the nuclear stain bis-benzamide.

Buspirone had similar differentiation-inducing effects on neural stem cells isolated from the striatum (Table 6). Concentrations of buspirone as low as 100 nM were able to promote differentiation significantly compared to untreated control cultures.

TABLE 2

Buspirone-induced Differentiation of Cerebellar Stem Cells

| Treatments | % Tuj 1 positive cells | % GFAP positive cells |
|---|---|---|
| Control | 28.3 ± 2.5 | 14.7 ± 0.9 |
| buspirone 10 nM | 40.0 ± 3.7 | 26.3 ± 3.7 |
| buspirone 30 nM | 41.2 ± 6.7 | 12.9 ± 1.9 |
| buspirone 100 nM | 33.1 ± 2.6 | 20.6 ± 5.2 |
| buspirone 300 nM | 26.1 ± 3.9 | 21.4 ± 4.6 |
| buspirone 1000 nM | 21.9 ± 3.9 | 27.0 ± 9.0 |

TABLE 3

Cerebellar Stem Cells

| Treatments | % Tuj 1 positive cells |
|---|---|
| control | 24.1 ± 3.3 |
| buspirone 10 nM | 30.7 ± 2.33 |
| buspirone 30 nM | 37.4 ± 2.6 |
| buspirone 100 nM | 46.6 ± 3.8 |
| buspirone 1000 nM | 40.3 ± 2.8 |

TABLE 4

Cerebellar Stem Cells

| Treatments | % TuJ1 positive cells |
|---|---|
| control | 19.1 ± 1.0 |
| buspirone 500 nM | 56.8 ± 7.1 |

TABLE 5

Cerebellar Stem Cells

| Treatments | % TuJ1 positive cells |
|---|---|
| control | 24.1 ± 2.6 |
| buspirone 100 nM | 54.4 ± 2.1 |
| buspirone 500 nM | 64.8 ± 2.1 |
| buspirone 10 µM | 67.9 ± 10.2 |
| buspirone 100 µM | 68.5 ± 6.5 |

TABLE 6

Differentiation of Striatal Stem Cells

| Treatments | % TuJ1 positive cells |
|---|---|
| control | 24.1 ± 2.6 |
| buspirone 100 nM | 54.4 ± 2.1 |
| buspirone 500 nM | 64.8 ± 2.1 |
| buspirone 10 µM | 67.9 ± 10.2 |
| buspirone 100 µM | 68.5 ± 6.5 |

Ligands for 5HT1A receptor induce neuronal differentiation of neural stem cells. To evaluate whether 5HT1A receptor ligands other than buspirone also accelerate differentiation of neural stem cells into neurons, neural stem cells were treated with buspirone, 5 µM serotonin (5HT), the natural ligand for the 5HT1A receptor, and an unrelated compound, vasoactive intestinal peptide (VIP) that is known to induce neuronal differentiation but does not bind to 5HT1A receptors. Untreated cells were used as a negative control. Results are presented in FIG. 2.

Figure 2:
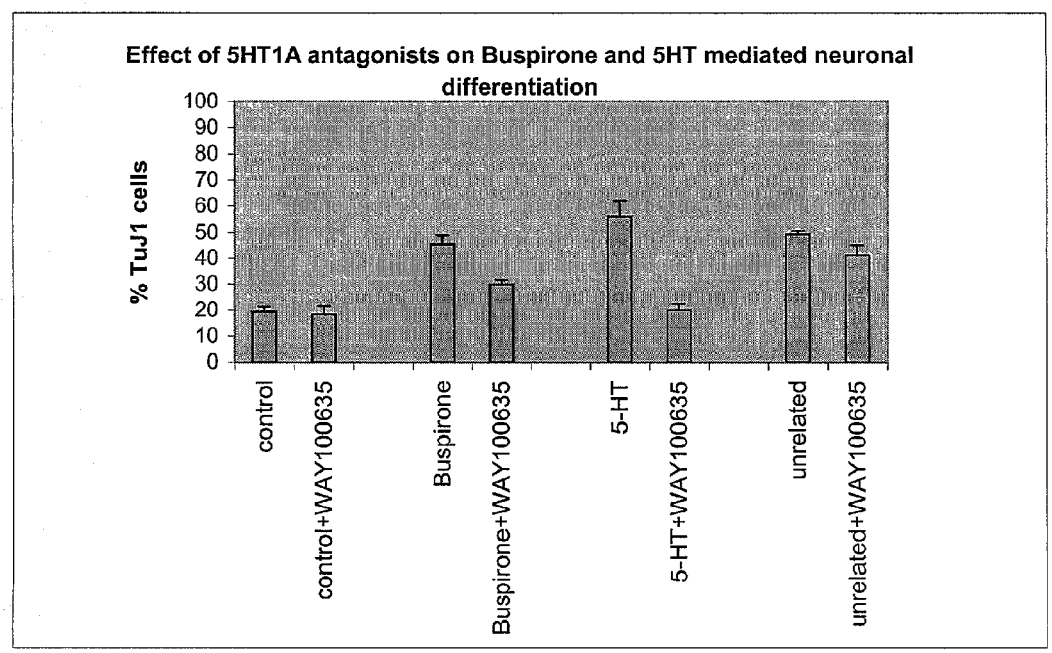
FIG. 2 demonstrates the effect of both a 5HT1A antagonist and an antagonist that does not bind to the 5HT1A receptor on buspirone (500 nM) and serotonin (5 µM)-mediated neuronal differentiation. Cells were treated with the drugs as shown in the presence or absence of the 5HT 1A antagonist WAY 100635 (10 nM), or vasoactive intestinal peptide

As shown in FIG. 2, cerebellar neural stem cells treated with 5HT 1A ligands buspirone and serotonin demonstrated accelerated differentiation of neurons by 50% and 60%, respectively compared with the untreated control, which demonstrated less than 20% differentiation (FIG. 2, lanes 3, 5 and 1 respectively). An unrelated differentiation-inducing agent, vasoactive intestinal peptide, was used as a positive control (FIG. 2, lane 7). Importantly, signaling through the 5HT1A receptor is demonstrated to be responsible for the accelerated neuronal differentiation induced by buspirone and serotonin, as simultaneous addition of a 5HT1A antagonist (WAY100635) to buspirone- or serotonin-treated cultures inhibited neuronal differentiation induced by buspirone or serotonin (FIG. 2, lanes 4 and 6). Supporting this mechanism, addition of WAY100635 to cells treated with a differentiation-inducing compound that does not bind to 5HT1A did not prevent or inhibit neuronal differentiation (FIG. 2, lane 8).

Figure 4A:
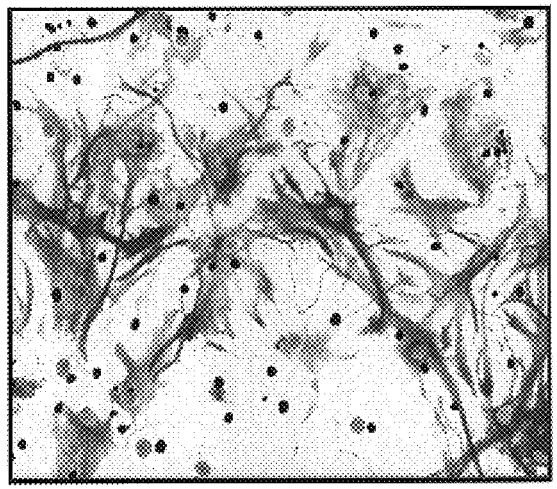
FIGS. 4A–B show immunostaining of rat cerebellar stem cells treated with either a solvent (FIG. 4A) or 100 nM buspirone (FIG. 4B). Astrocytic differentiation is estimated by cells which stain positive for GFAP (red), while total cell number is determined by counting the bis-benzamide-stained nuclei (blue). The bar in B represents 100 microns.
Figure 4B:
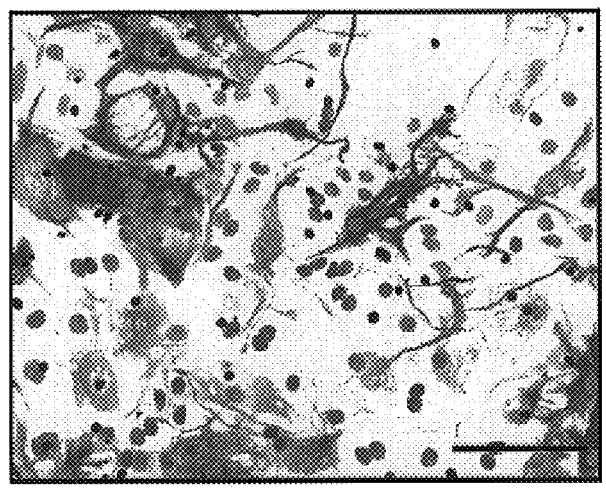

Buspirone Inhibits the Differentiation of Neural Stem Cells Into Astrocytes. To evaluate whether buspirone affected differentiation of neural stem cells into other neural cell types such as astrocytes, the buspirone-treated cerebellar cell cultures described above were subjected to immunofluorescence using a monoclonal antibody against an astrocyte-specific marker, glial fibrillary acidic protein, or GFAP. As for neuronal immunofluorescence, the photographs in FIG. 4 represent results from experiments of the rat cereballar cultures treated with either solvent (FIG. 4A) or buspirone (100 nM-FIG. 4B). The red color demonstrates positive staining for GFAP, while the blue stain represents the total number of cells in the culture as indicated by the nuclear stain bis-benzamide.

As shown in FIG. 1B and FIG. 4, treatment with concentrations of buspirone ranging from 30 nM to 1 µM does not have any appreciable reproducible effects on astrocytic differentiation.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all numerical values, provided for description, are approximate.

All patents, patent applications, publications, and other materials cited herein are hereby incorporated herein reference in their entireties. In case of conflicting terminology, the present disclosure controls.

What is claimed is:

1. A method for preparing a population of mammalian neural cells enriched with neuronal cells comprising the step of exposing a population of mammalian neural stem cells expanded in culture in the presence of bFGF to a 5HT1A agonist in vitro in the absence of bFGF in an amount and at a frequency of exposure sufficient to induce differentiation of said stem cells to express a neuronal cell marker.

2. The method of claim 1 wherein said mammalian neural stem cells are selected from the group consisting of adult, juvenile, and fetal neural stem cells.

3. The method of claim 1 wherein said population of mammalian neural cells comprises at least 90% neural stem cells.

4. The method of claim 1 wherein the amount of said 5HT1A agonist is within a range of between about 1 nM and about 100 μM.

5. The method of claim 1 wherein said frequency is daily.

6. The method of claim 1 wherein said frequency is every other day.

7. The method of claim 1 wherein the exposing step comprises adding said 5HT1A agonist to a culture medium and culturing said mammalian neural stem cell population in said medium.

8. The method of claim 1, wherein the duration of the exposure to said 5HT1A agonist continues for a period of time within the range between about 2 and about 30 days.

9. The method of claim 6 wherein the period of time is about 6 days.

10. The method of claim 1, wherein the neural stem cells are human neural stem cells.

11. The method of claim 10, wherein the human neural stem cells are fetal human neural stem cells.

12. The method of claim 1, wherein the mammalian neural stem cells are rat neural stem cells.

13. The method of claim 1, wherein the neural stem cells are derived from a primary culture comprising the cortex, cerebellum or striatum neural stem cells.

14. The method of claim 1 wherein the 5HT1A agonist is selected from the group consisting of buspirone, serotonin, 5 methoxy N,N dimethyltryptamine, S(−) pindolol, ipsapirone, 3-(2-dimethylaminoethyl)-5-methoxyindole, 1-[3-(3,4-methylene-dioxyphenoxy, 8-Hydroxy-DPAT hydrobromide, (±)-8-Hydroxy-2-dipropylaminotetralin, 8-[4-(1,4-Benzodioxan-2-ylmethylamino)butyl]-8-azaspiro[4.5]decane-7,9-dione, and [(+)-R)-2-cyano-N,N-dipropyl-8-amino-6,7,8,9-tetrahydro-3H-benz[e]indole].

15. The method of claim 14, wherein the 5HT1A agonist is buspirone.

16. The method of claim 14, wherein the 5HT1A agonist is serotonin.

17. The method of claim 15, wherein the amount of buspirone is about 100 nM.

18. The method of claim 16, wherein the amount of serotonin is about 5 μM.

19. The method of claim 1, further comprising exposing the mammalian neural stem cell population to Brain-Derived Neurotrophic Factor (BDNF).

20. The method of claim 3, wherein the amount of BDNF is in a range of about 1 ng/ml to about 50 ng/ml.

21. The method of claim 3, wherein the proportion of said stem cells differentiated into neurons is at least 30%.

22. The method of claim 21, wherein the proportion of neurons is 50%.

23. A method for preparing a population of mammalian neural cells enriched with neuronal cells comprising the step of exposing a population of mammalian neural stem cells with buspirone in vitro in an amount and at a frequency of exposure sufficient to induce differentiation of said stem cells to express a neuronal cell marker.

24. The method of claim 23, wherein the amount of buspirone to which the neural stem cells are exposed is about 100 nM to about 100 μM.

25. The method of claim 1 wherein the amount of bFGF is about 10 ng/ml/day.

26. The method of claim 25, wherein the neural stem cells are expanded for about 3–4 days.

* * * * *